United States Patent
Poorter et al.

(10) Patent No.: US 9,513,384 B2
(45) Date of Patent: Dec. 6, 2016

(54) SEAMLESS TILING TO BUILD A LARGE DETECTOR

(71) Applicant: KONINKLIJKE PHILIPS N.V., Eindhoven (NL)

(72) Inventors: Tiemen Poorter, Heerlen (NL); Ronald Dekker, Valkenswaard (NL); Vincent Adrianus Henneken, Utrecht (NL); Nicolaas Johannes Anthonius Van Veen, Geldrop (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 189 days.

(21) Appl. No.: 14/356,553

(22) PCT Filed: Nov. 6, 2012

(86) PCT No.: PCT/IB2012/056176
§ 371 (c)(1),
(2) Date: May 6, 2014

(87) PCT Pub. No.: WO2013/068912
PCT Pub. Date: May 16, 2013

(65) Prior Publication Data
US 2014/0307850 A1  Oct. 16, 2014

Related U.S. Application Data

(60) Provisional application No. 61/556,870, filed on Nov. 8, 2011.

(51) Int. Cl.
*H01L 27/146* (2006.01)
*G01T 1/00* (2006.01)
(Continued)

(52) U.S. Cl.
CPC ............... *G01T 1/208* (2013.01); *G01N 23/04* (2013.01); *G01T 1/2018* (2013.01); *G01T 1/243* (2013.01);
(Continued)

(58) Field of Classification Search
CPC ........ G01T 1/2018; G01T 1/208; G01T 1/243; G01T 1/2928
See application file for complete search history.

(56) References Cited

U.S. PATENT DOCUMENTS 4,891,522 A   1/1990  Coon et al.
6,057,552 A   5/2000  Stettner et al.
(Continued)

FOREIGN PATENT DOCUMENTS

EP   1237141       9/2002
WO   03083944 A1  10/2003
WO   2010058335 A2  5/2010

OTHER PUBLICATIONS

M. Tamaki, et al., "Development of 4-Sides Buttable CdTe-ASIC Hybrid Module for X-Ray Flat Panel Detector", IEEE Transactions on Nuclear Science, vol. 56, No. 4, Aug. 2009, pp. 1791-1794.
(Continued)

*Primary Examiner* — David J Makiya
*Assistant Examiner* — Dani Fox

(57) ABSTRACT

A detector tile and a detector panel arrangement for providing a seamless detector surface with a continuous pixel array and with a reduced gap appearance includes a detector tile having a flat primary substrate and a surface layer with a circuitry arrangement. The surface layer is arranged on a front side of the primary substrate covering the primary substrate. The circuitry arrangement includes detector pixels providing a pixel array, where a connection opening is provided in the surface layer and the flat primary substrate
(Continued)

at least at one edge of the detector tile. The connection opening is leading from the surface layer to the rear of the substrate for guiding electrical connection elements between the front side and a rear of the detector tiles. The connection openings on opposing edges of the detector tile alternate, and the connection openings on adjacent edges of detector tiles alternate.

16 Claims, 8 Drawing Sheets

(51) Int. Cl.
      *G01T 1/208*     (2006.01)
      *G01T 1/20*      (2006.01)
      *G01T 1/24*      (2006.01)
      *G01T 1/29*      (2006.01)
      *G01N 23/04*    (2006.01)

(52) U.S. Cl.
    CPC ....... *G01T 1/2928* (2013.01); *H01L 27/14687* (2013.01)

(56) References Cited

U.S. PATENT DOCUMENTS

| | | | |
|---|---|---|---|
| 6,204,087 | B1 | 3/2001 | Parker et al. |
| 2002/0154259 | A1* | 10/2002 | Freidhoff ............... G09G 3/20 349/73 |
| 2005/0121598 | A1 | 6/2005 | Nygard |
| 2005/0139757 | A1 | 6/2005 | Iwanczyk et al. |
| 2005/0286682 | A1 | 12/2005 | Tkaczyk et al. |
| 2006/0192087 | A1* | 8/2006 | Kuszpet ............... G01T 1/2928 250/214 R |
| 2011/0192983 | A1 | 8/2011 | Yu et al. |

OTHER PUBLICATIONS

G. Vogtmeier, et al., "CMOS Compatible through Wafer Interconnects for Medical Imaging Detectors", 2007 IEEE Nuclear Science Symposium Conference Record, M18-166, pp. 3430-3435.

* cited by examiner

SEAMLESS TILING TO BUILD A LARGE DETECTOR

CROSS-REFERENCE TO PRIOR APPLICATIONS

This application is the U.S. National Phase application under 35 U.S.C. §371 of International Application Serial No. PCT/IB2012/056176, filed on Nov. 6, 2012, which claims the benefit of U.S. Application Ser. No. 61/556,870, filed on Nov. 8, 2011. These applications are hereby incorporated by reference herein.

FIELD OF THE INVENTION

The present invention relates to a detector tile, a detector panel arrangement, an X-ray detector, an X-ray imaging system, and a method for providing a detector tile for a seamless detector surface with a continuous pixel array.

BACKGROUND OF THE INVENTION

To create large area of detectors, for example large area of X-ray detectors, a number of detector tiles is combined. For example, WO 2010/058335 A2 describes the alignment of a multi-tile detector. To bring the electrical connections from the active front side to the back of each tile, it is possible to provide the tiles with a distance to each other leading to more or less through-going linear gaps along adjacent sides between the individual tiles. However, such gaps prevent a continuous detector surface. The gaps rather result in line structures across the whole detector surface. Therefore, the gaps are unacceptable in, for example, medical applications.

SUMMARY OF THE INVENTION

There may be a need to provide detector tiles to build a large area detector with reduced gap appearance.

The object of the present invention is solved by the subject-matter of the independent claims, wherein further embodiments are incorporated in the dependent claims.

It should be noted that the following described aspects of the invention apply also for the detector tile, the detector panel arrangement, the X-ray detector, the X-ray imaging system, and the method for providing a detector tile for a seamless detector surface with a continuous pixel array.

According to a first aspect of the present invention, a detector tile is provided, comprising a flat primary substrate and a surface layer with a circuitry arrangement. The surface layer is arranged on a front side of the primary substrate covering the primary substrate. The circuitry arrangement comprises a number of detector pixels providing a pixel array. At least one connection opening is provided in the surface layer and the flat primary substrate at least at one edge of the detector tile, which connection opening is leading from the surface layer to the rear of the substrate for guiding electrical connection elements between the front side and the rear of the detector tiles. At all circumferential edges of the detector tile, the surface layer comprises at least portions with pixels, which portions extend to the edge.

For example, the detector tile is a tile for an X-ray detector.

According to a further example, the detector tile is a tile for a camera sensor for electromagnetic waves in the visible light range, or in the infrared range, for example.

The term "rear of the substrate" refers to the area, i.e. the volume, behind the substrate, and not only to the actual rear side of the substrate itself.

The connection openings may be provided as cutouts, for example as slots, grooves, or slits, wherein the openings can be provided with different opening ratios, for example as broad or narrow slots, and also with different depths.

According to an example, a number of connection openings are provided along one edge of the substrate, wherein the connection openings have an opening width in the direction of the detector's edge, and wherein the connection openings are arranged in a distance, which is at least equal to the opening width.

According to a further exemplary embodiment, a first number of first connection openings is provided on one edge of the substrate and at least a second number of second connection openings is provided on an opponent edge of the substrate: The first number is provided with a first offset and the second number is provided with a second offset, wherein the first and the second offset are arranged such that, when projected onto each other, first and second connection openings are alternating.

For example, a further number, for example a third number of further connection openings is provided on one further edge of the substrate, for example on a third edge, and at least one still further number, for example a fourth number, of still further connection openings is provided on an opponent still further edge of the substrate, for example on a fourth edge.

According to a further exemplary embodiment, peripheral electronics are provided on a secondary substrate arrangement, wherein the secondary substrate arrangement is arranged on the rear of the detector tile. As electrical connection elements, at least one connecting wiring is provided comprising a number of electric leads connecting the circuitry arrangement on the surface layer with the peripheral electronics. The at least one connecting wiring is guided through the at least one connection opening.

For example, the secondary substrate arrangement may comprise one or more secondary substrate elements, e.g. 2, 3, 4 or more elements.

According to a further exemplary embodiment, a number of connection openings are provided at least on two sides of the detector tile, wherein the connection openings are arranged such that the detector tile is abuttable on at least three sides, preferable on all sides, for providing a seamless detector surface.

According to a further exemplary embodiment, the pixel array is provided with a detector tile grid; and wherein edge pixels arranged along at least one side of the detector tile are provided with a reduced size in a direction transverse to the edge such that the outmost edge of the detector tile is arranged within the respective grid field of the pixel.

This allows the arrangement of detector tiles abutting each other but still providing a continuous overall pixel grid.

According to a second aspect of the invention, a detector panel arrangement is provided, comprising at least two detector tiles according to one of the above mentioned examples. The detector tiles are arranged in a common plane abutting each other such that a seamless detector surface is provided with a continuous pixel array, wherein the continuous pixel array is only partially interrupted by the connection openings.

According to a third aspect of the present invention, an X-ray detector is provided, comprising a detector panel arrangement according to the above mentioned example and an X-ray conversion layer in front of the detector panel. The X-ray conversion layer is configured to provide signals to the detector panel upon being radiated by X-rays. The signals are adapted to electrically activate the pixels in the surface layer of the detector tiles.

According to an exemplary embodiment, the X-ray conversion layer is of a direct conversion type, wherein for each pixel of the surface, the X-ray radiation is converted into an electrical signal supplied to the respective pixel.

According to a further exemplary embodiment, the X-ray conversion layer is of a scintillator type, wherein the pixels in the pixel array each comprise a light-sensing element to detect light generated in the scintillator layer by X-ray influence.

According to a fourth aspect of the present invention, an X-ray imaging system is provided, comprising an X-ray source, an X-ray detector according to one of the above mentioned examples, and a processing unit. The processing unit is configured at least to correct for missing image information in the area of the connection openings of the continuous pixel array.

According to a fifth aspect of the present invention, a method for providing a detector tile for a seamless detector surface with a continuous pixel array is provided, comprising the following steps:
a) Providing a wafer comprising a flat primary substrate and a surface layer with a circuitry, the wafer comprising a first portion with a circuitry arrangement, which comprises a number of detector pixels providing a pixel array on the surface layer, and at least one second portion with peripheral electronics, wherein the first portion is separated from the at least one second portion by at least one intermediate portion.
b) Forming a patterned layer of at least one connecting wiring comprising a number of electric leads, the electric leads connecting the circuitry arrangement with the pixels with the peripheral electronics, wherein the patterned layer is formed on the front surface of the wafer bridging the intermediate portion.
c) Removing wafer material in the at least one intermediate portion.
d) Removing wafer material of the first portion such that at least one connection opening is provided in the surface layer and the flat primary substrate at least at one edge of the detector tile, which connection opening is leading from the surface layer to the rear of the substrate for guiding the electric leads between the pixels and the peripheral electronics.
e) Moving the at least one second portion with peripheral electronics to the rear of the wafer, wherein the at least one connecting wiring is guided through the at least one connection opening.

According to an aspect of the present invention, a detector tile is provided in which channel-like openings are provided along the edge to receive the wiring, which wiring is provided to connect the front side of the detector tile, i.e. the circuitry arrangement comprising the pixel array, with electronics and other connections on the rear of the detector tile. Thus, a continuous detector surface or detector area is possible by abutting a number original detector tiles according to the present invention, wherein the pixel arrays of the detector tiles form a large pixel area, which is capable of providing continuous image information except for the locations where the openings are provided. Thus, any kind of gap between adjacent detector tiles is avoided. By providing the openings an in alternating manner, it is possible to reduce the areas where a pixel is replaced with an opening to a minimum such that the missing image data can easily be replaced by a correction algorithm.

According to a further aspect of the present invention, by providing a number of connection positions, i.e. a number of connection openings, a number of small size lead bundles can be provided such that in an optimal case only one pixel is used for the connection opening.

According to a still further aspect of the present invention, the connection wiring is provided as a flexible structure, such that the circuitry arrangement on the substrate layer of the detector tile as well as the peripheral electronics needed for the circuitry arrangement, can be provided in a common manufacturing procedure, wherein the electrical connections are acting like a hinge, with which the peripheral electronics are attached to the detector tile itself.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
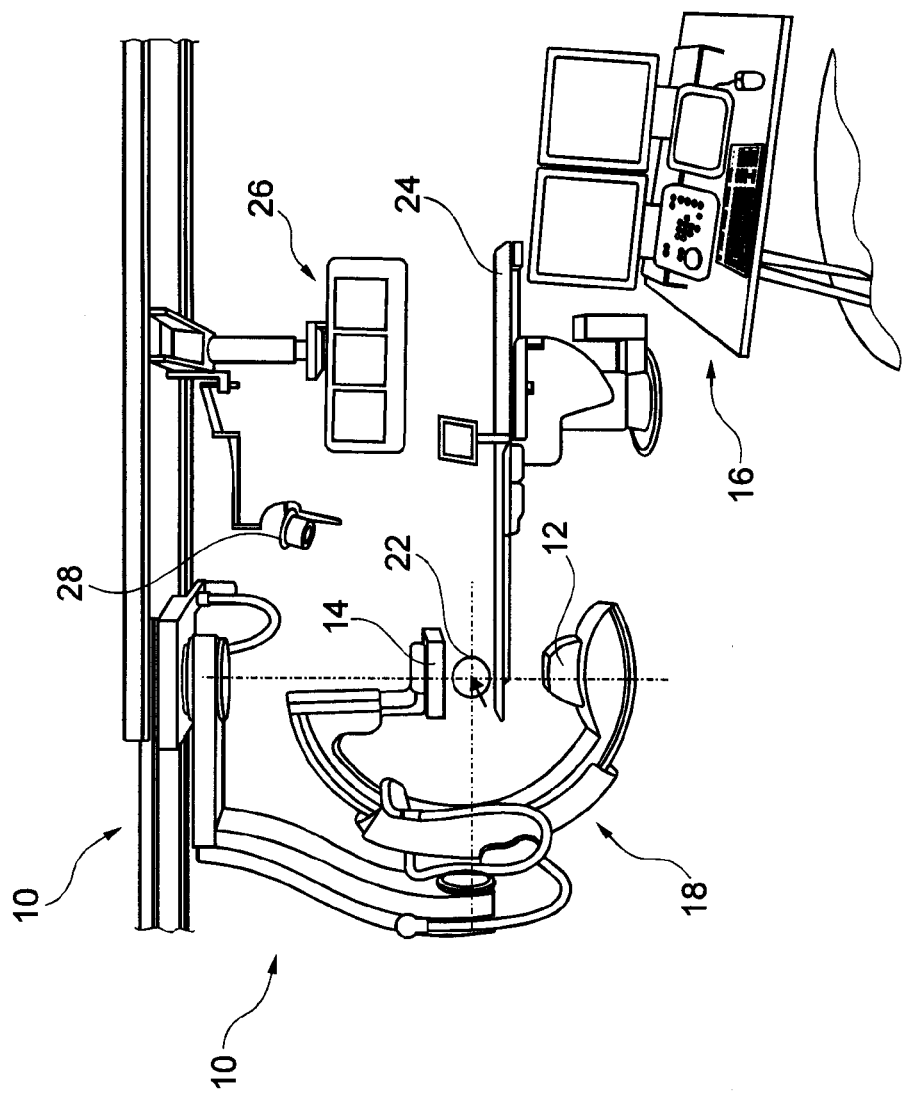
FIG. 1 illustrates an X-ray imaging system according to an exemplary embodiment of the invention.

FIG. 1 shows an X-ray imaging system 10 comprising an X-ray source 12 and an X-ray detector 14, as well as a processing unit 16.

The X-ray imaging system 10 is shown as a C-arm type system, wherein the X-ray source 12 and the X-ray detector 14 are provided on opposing ends of a C-arm structure 18, which is movably mounted by a ceiling support 20 such that the X-ray source 12 and the X-ray detector 14 can be moved around an object 22, for example a patient. To support the patient, a patient table 24 is provided, which can be adaptable in a number of directions, for example in height and along the horizontal direction. Further, a display unit 26 is shown in the vicinity of the C-arm structure 18, as well as a schematically indicated lighting component 28.

The processing unit 16 is configured at least to correct for missing image information in the area of connection openings of a continuous pixel array, which will be described further below. Of course, the processing unit can also be configured for other tasks, such as controlling the X-ray source and X-ray detector, the movement of the C-arm structure 18, and to control the display unit 26, for example.

The X-ray detector 14 is provided as an X-ray detector according to one of the below mentioned examples.

Figure 2:
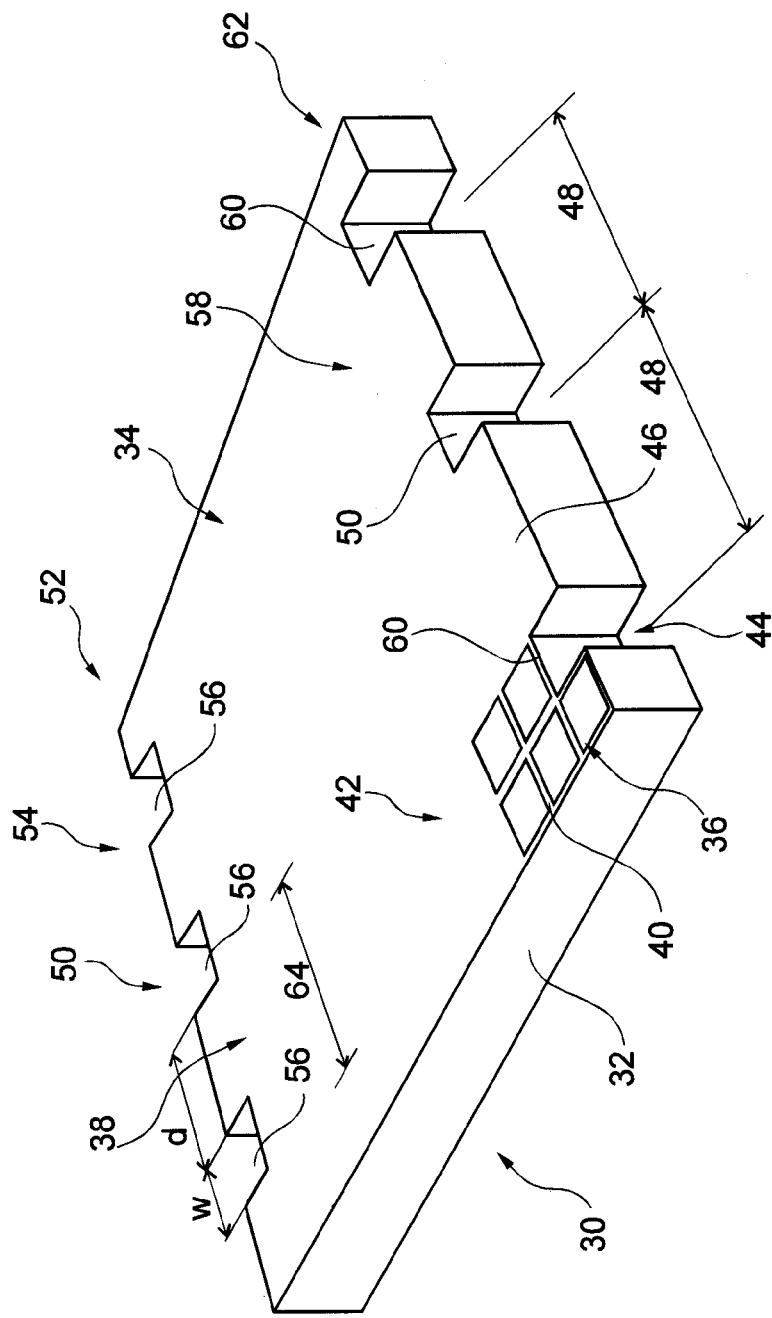
FIG. 2 schematically illustrates a detector tile according to an exemplary embodiment of the invention.

Before further describing the X-ray detector 14, it is referred to FIG. 2 showing a detector tile 30 according to the present invention for the detector 14. The detector tile 30 comprises a flat primary substrate 32 and a surface layer 34 with a circuitry arrangement 36. The surface layer 34 is arranged on a front side 38 of the primary substrate 32 covering the primary substrate. The circuitry arrangement 36 comprises a number of detector pixels 40 providing a pixel array 42.

According to the present invention, at least connection opening 44 is provided in the surface layer 34 and the flat primary substrate 32 at least at one edge of the detector tile, which connection opening 44 is leading from the surface layer 34 to the rear of the substrate for guiding electrical connection elements (not further shown in FIG. 2) between the front side and the rear of the detector tiles. At all circumferential edges of the detector tile, the surface layer comprises at least portions 46 with pixels, which portions extend to the edge.

The detector tile may be a tile for an X-ray detector.

The detector tile may also be a tile for a camera sensor for electromagnetic waves, for example in the visible light range, or for infrared waves.

The term "rear of the substrate" refers to the area behind the substrate, and does not only refer to the actual rear side of the substrate itself.

The substrate layer may comprise a circumferential edge with pixels interrupted only partially by the connection openings 44. The substrate layer may extend up to the circumferential edges of the front side of the substrate. The connection openings may be provided as cutouts, for example as slots, grooves, or slits. The slots can be provided with different opening ratios, for example for broad or narrow slots, and also with different depths. For example, the at least one connection opening 44 consumes the area of a single pixel. The at least one connection opening 44 may also consume the area of a small group of pixels.

The connection openings may be provided in a repeating pitch 48, as schematically shown. The repeating pitch may also be referred to as a repeating offset or a repeating distance.

According to a further example, also shown in FIG. 2, a number 50 of connection openings 44 is provided along one edge 52 of the substrate, wherein the connection openings have an opening width W in the direction of the detector's edge, and wherein the connection openings are arranged in a distance D, which is at least equal to the opening width, preferably larger than the opening width.

According to a further example, as also shown in FIG. 2, at least a first number 54 of first connection openings 56 is provided on one edge, for example the edge 52. At least a second number 58 of second openings 60 is provided on an opponent edge 62. The first number 54 is provided with a first offset 64, and the second number is provided with a second offset, for example the offset 48. The first and the second offset are arranged such that when projected onto each other, first and second connection openings are alternating.

According to a further example, not further shown, also further numbers of further connection openings may be provided on further edges. For example, a third number of further connection openings is provided on a third edge, and at least one still further number, for example a fourth number, of still further connection openings is provided on an opponent fourth edge of the substrate. According to a further example, shown in FIG. 3, peripheral electronics 65 are provided on a secondary substrate arrangement 66. The secondary arrangement 66 is arranged on the rear of the detector tile. In other words, in FIG. 3, the front side of the detector tile is facing upwards, such that the area below the detector tile is a rear of the detector tile. As electrical connection elements, at least one connecting wiring 68 is provided comprising a number of electric leads 70 connecting the circuitry arrangement 36 (not further shown in FIG. 3) on the surface layer 34 with the peripheral electronics 65. The at least one connecting wiring 68 is guided through the at least one connection opening 44.

The connecting wiring 68 comprises connections for the pixels and connection for further circuitry connection, such as for biasing purposes, for readout signal lines etc.

The electrical leads 70 may be provided on a flexible foil structure, for example a polyimide foil or a polyimide multilayer stack, for example, with a polyimide layer, a metal layer, and a further polyimide layer. For each connected detector pixel, the at least one connecting wiring 68 may comprise one electrical lead, i.e. each detector pixel may be connected by one of the electrical leads.

According to a further example, each pixel is connected with multiple connections, i.e. multiple electrical leads. According to a further example, more than one pixel is connected to the peripheral electronics 65 with one electrical lead 70, for example by using a multiplexing technique. Still further, one connecting wiring may comprise a number of electrical leads or channels. A number of connecting wirings and a respective number of connection openings may be provided, wherein one connecting wiring passes through one connection opening.

It is further noted that within the detector tile area, for example in the middle or central part, one or more pixels can be sacrificed for circuit purposes; for example, for providing circuits for multiplexing signals from different pixels.

For example, a tile with 100×100 pixels is provided, with 10000 connection leads. Providing every second pixel on two opposing sides as a connection opening, altogether 100 connection openings are provided, each for 100 leads. This would mean to sacrifice only 1% of the detector surface to achieve a seamless detector surface.

The secondary substrate arrangement 66 comprises at least one secondary substrate portion 72 on which electronic circuits (not shown) are provided. The secondary substrate and the primary substrate may have the same composition. However, the primary and secondary substrate may be provided with different surface layers with different circuitry. According to a further example, the secondary substrate and the primary substrate are made from the same material.

For example, the primary substrate is a crystalline silicon-based substrate. According to a further example, the primary substrate may be provided as a silicon-on-insulator substrate.

Figure 3:
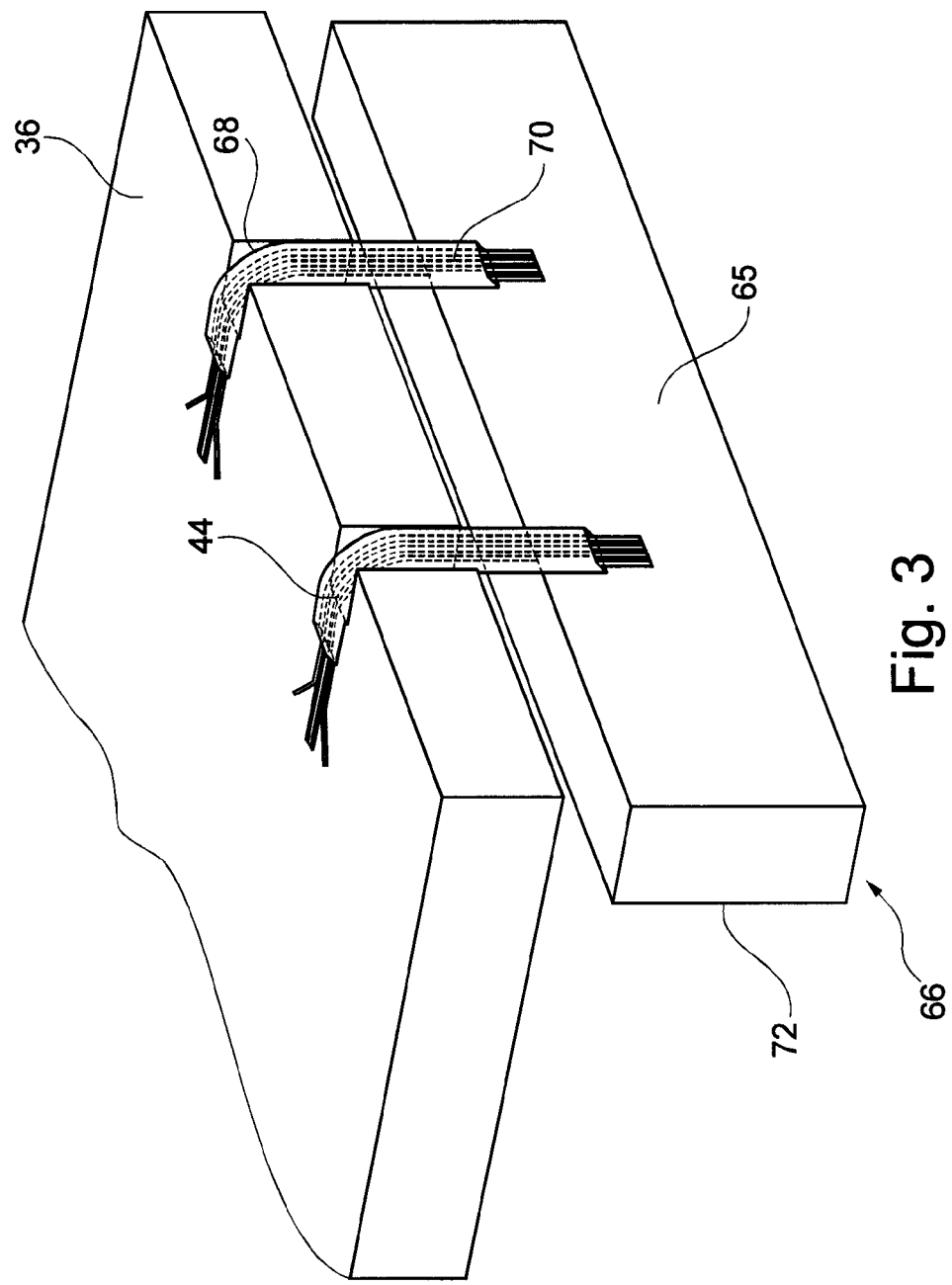
FIG. 3 shows a further example of a detector tile according to the present invention.
Figure 4:
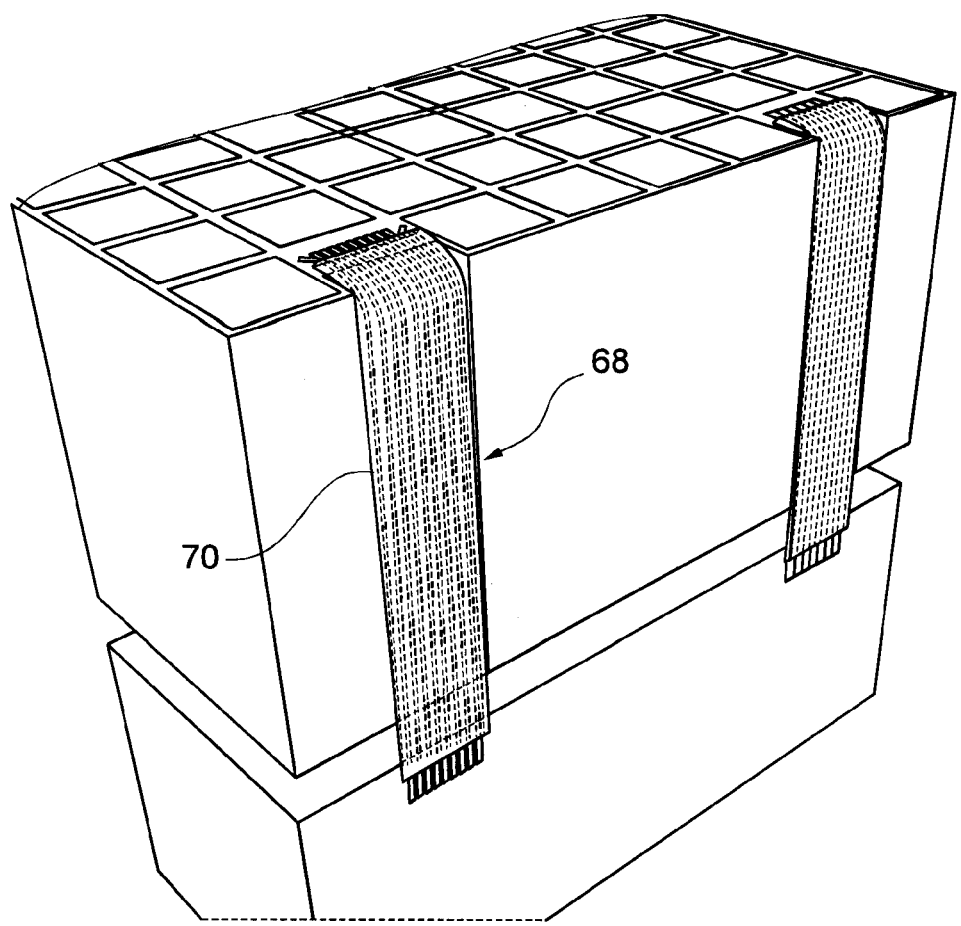
FIG. 4 shows a further exemplary embodiment of a detector tile according to the present invention.

FIG. 4 shows a more detailed perspective view of the connecting wiring 68 showing a number of electrical leads. As also indicated in FIG. 3, the connecting wiring 68 basically runs through the connection opening and contacts the top surface, i.e. the surface layer, of the detector tile and the sideward facing surface of the secondary substrate portion. The individual electrical leads are then connected to not further shown electrical leads running from the connecting wiring 68 to the respective pixel arrangement, etc.

Figure 5:
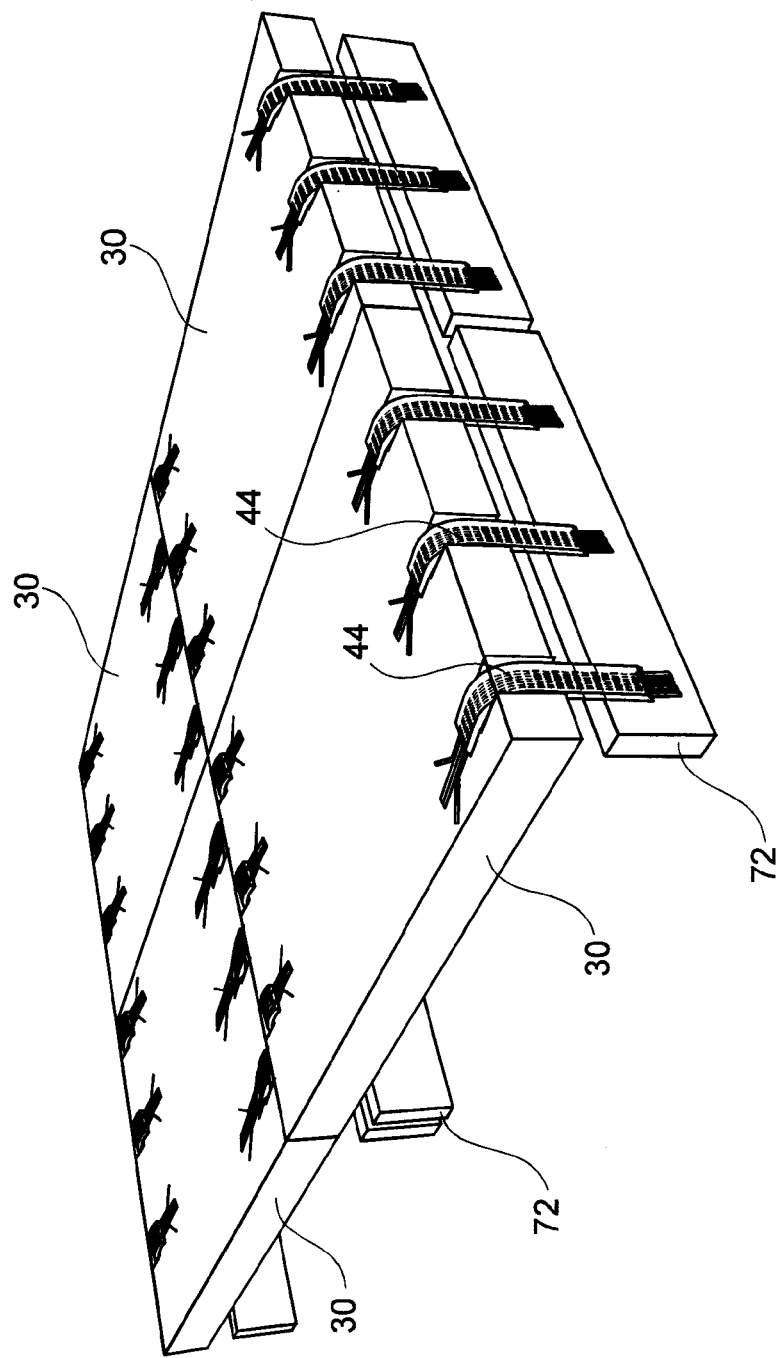
FIG. 5 shows a further exemplary embodiment of a detector panel arrangement.

FIG. 5 shows a number of different aspects in combination. However, it is explicitly noted that the below mentioned features can also be provided separated from each other.

As indicated in FIG. 5, a first and a second secondary substrate portion 72 is provided for each detector tile 30. For example, the secondary substrate portions are provided on opposing edges of the detector tile.

According to a not further shown example, two secondary substrate portions 72 are provided on two sides, respectively edges of one detector tile 30. However, also one or even more than two secondary substrate portions may be provided according to the present invention. For example, three or four secondary substrate portions are arranged along, i.e. below the edges of the detector tile 30.

As also shown in FIG. 5, a number of connection openings 44 is provided on two sides of the detector tile 30. For example, this can also be provided on one side, or more than two sides. For example, the connection openings are arranged such that the detector tile is abuttable on at least three sides for providing a seamless detector surface.

When providing the connection openings 44 on two opposing sides, leaving one side of the detector tile without openings, the detector tile could be arranged in relation to an adjacent detector tile in a so-called chessboard pattern, i.e. where the adjacent detector tile is rotated around 90° such that an edge with connection openings is contacting an edge without connection openings.

According to the example shown in FIG. 5, adjacent detector tiles 30 are arranged such that edges on which connection openings 44 are provided, are arranged in an abutting manner such that edges where no openings are provided are contacting edges where also no openings are provided.

The term "abuttable" relates to an adjoined arrangement of the detector tiles, for example with two or more, preferably four or more detector tiles, for example as shown in FIG. 5.

Figure 6:
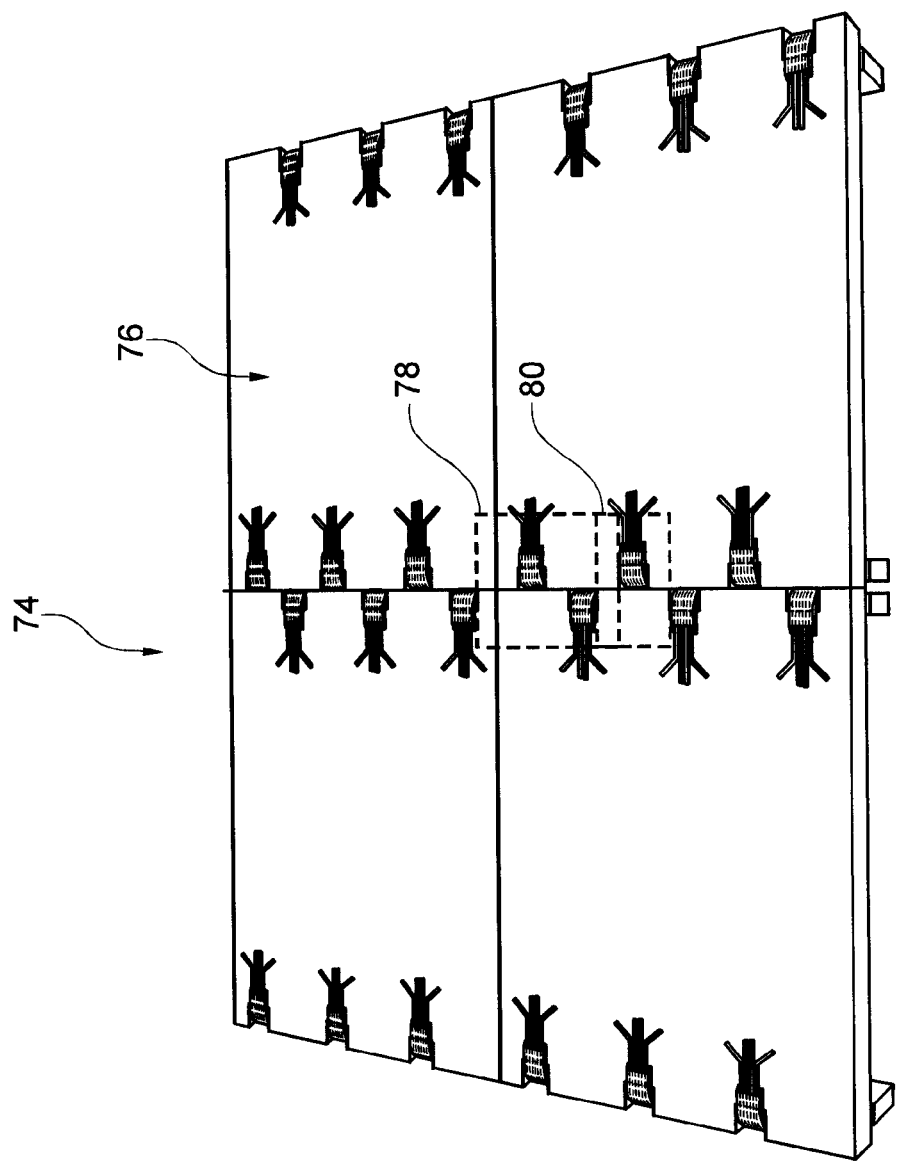
FIG. 6 shows a further exemplary embodiment of a detector panel arrangement.

The present invention also relates to a detector panel arrangement 74, for example shown in FIG. 6 from a view from further above than the example shown in FIG. 5. The detector panel arrangement 74 according to the present invention comprises at least two detector tiles 30 according to one of the above mentioned examples. The detector tiles are arranged in a common plane abutting each other such that a seamless detector surface 76 is provided with a continuous pixel array. The continuous pixel array is only partially interrupted by the connection openings. It must be noted that the pixels themselves are not shown in FIGS. 5 and 6, for example.

Further, adjacent detector tiles each comprise adjacent pixel portions arranged such that a transition portion, for example as indicated with a first dotted frame 78, is provided with a continuous pixel array sub-portion, as indicated with a second dotted frame 80.

It is thus ensured that a detector is capable of recording image information without gap-like interruptions, but only with point-like interruptions due to the connection openings. The continuous pixel array sub-portions ranging from one tile to the adjacent tile provides continuous image information across the detector tile boundaries or connecting edges.

As also shown in FIG. 6, the detector tiles are each provided with a number of connection openings, wherein the connection openings of adjacent detector tiles are arranged displaced to each other.

However, it is also possible to provide a number of connection openings such that adjacent detector tiles have also adjacent connection openings. However, by providing connection openings of adjacent tiles in contact with each other, the effective size of the so-to-speak blackout portion of the detector surface is increased. It is noted that the smaller the individual effective blackout area is, the better is the result of a correction algorithm.

Thus, preferably first and second connection openings are provided next to each other without overlapping each other.

Figure 7:
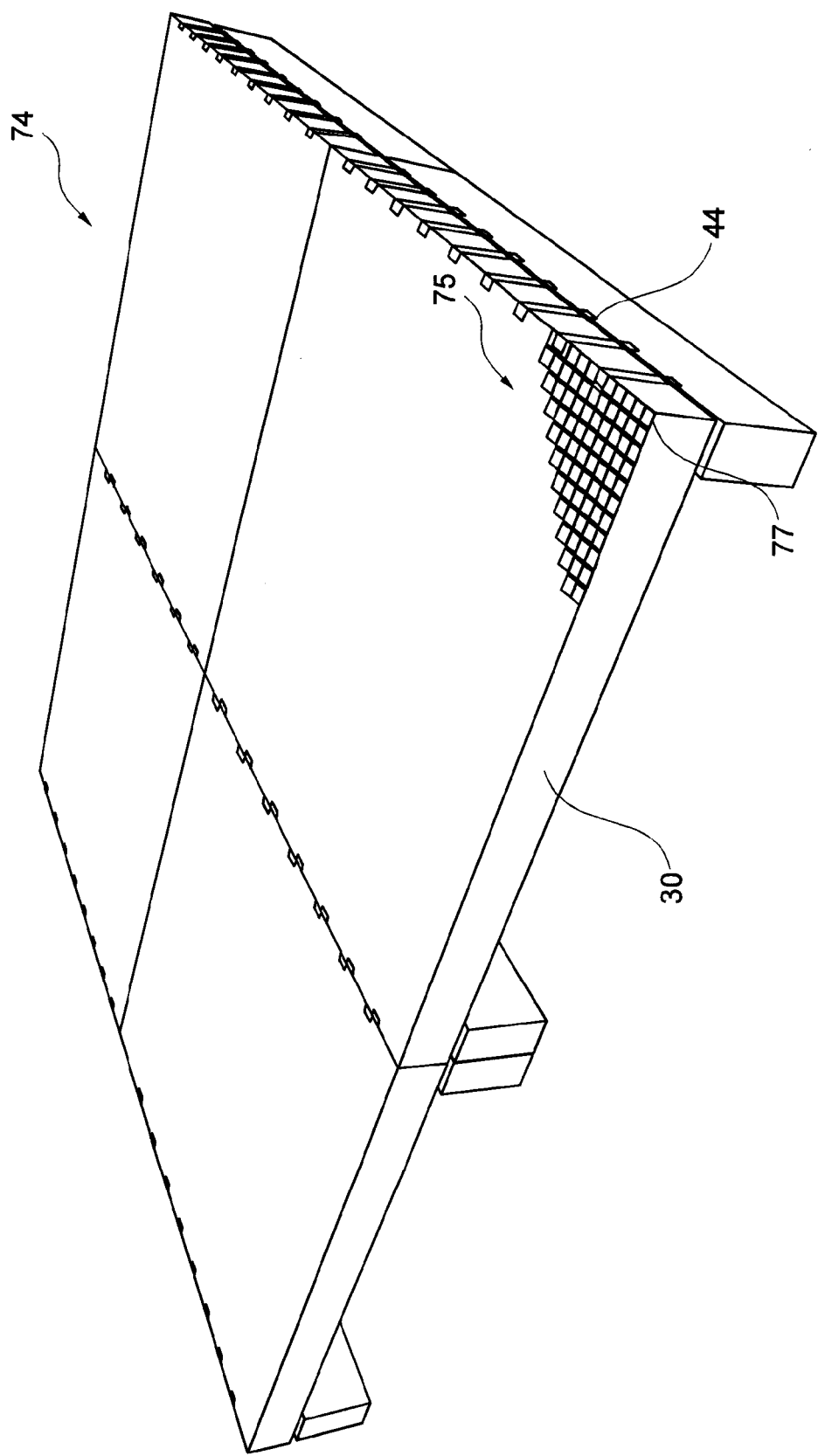
FIG. 7 shows a further exemplary embodiment of a detector panel arrangement according to the present invention.

For a more detailed understanding, FIG. 7 shows an indication of pixels in one corner only, and a number of connection openings 44 along opposing edges of each detector tile 30. As can be seen, the ratio of detector pixels providing image information to the connection openings is rather large, i.e. the amount of detector pixels used for arranging the connection openings is very low compared to the overall surface of one detector tile, and of course also when compared to the overall surface of the whole detector arranged 74.

A further aspect is also shown in FIG. 7, although also provided in combinations with other features of other examples. According to this aspect, the pixels are provided in the pixel array 42, which is provided with a detector tile grid 75. Edge pixels 77 arranged along at least one side of the detector tile are provided with a reduced size in a direction transverse to the edge such that the outmost edge of the detector tile is arranged within the respective grid field of the pixel. As a result, the pixels of adjacent tiles are provided in a common pixel grid, also referred to as single pixel grid. The size reduction may be provided in the dimension of a few microns, for example.

Figure 8:
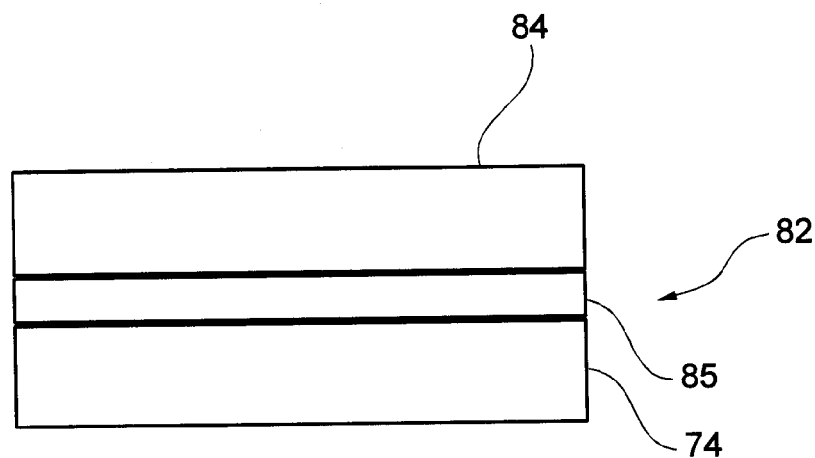
FIG. 8 shows an X-ray detector according to an exemplary embodiment of the present invention.

As indicated in relation with FIG. 1, according to the present invention, an X-ray detector 82 is provided, comprising a detector panel arrangement 74 according to one of the above mentioned examples, and an X-ray conversion layer 84 in front of the detector panel. FIG. 8 shows a very schematic cross-section, where X-ray radiation is coming from above, i.e. the conversion layer 84 is arranged, in relation to the drawing, on top of the detector panel arrangement 74. The X-ray conversion layer 84 is configured to provide signals to the detector panel upon being radiated by X-rays, wherein the signals are adapted to electrically activate the pixels in the surface layer of the detector tiles.

Between the conversion layer 84 and the detector panel arrangement 74, an intermediate layer 85, or intermediate space is provided.

According to a further example, not shown, the X-ray conversion layer 84 is of a direct conversion type, wherein for each pixel of the surface, the X-ray radiation is converted into an electrical signal supplied to the respective pixel.

For example, for a direct conversion layer, the intermediate layer 85 comprises bump-bonds, the polyimide multilayer stack, etc.

The electrical signal may be provided by conversion material arranged on the pixel of the surface layer.

According to a further example, the electrical signal is provided by conversion material arranged on the pixel of the surface layer, wherein between the pixel and the conversion material, an isolating layer is provided, and wherein the pixels are provided with an electrode passing through the isolating layer up to the surface, providing electrical connection with the conversion material.

Each pixel may thus have an electrical finger sticking out through a polyimide stack to stick out of the surface to contact direct conversion material.

According to a further example, a conversion layer is provided in form of a conversion tile with a continuous layer for each detector tile. According to a further example, a conversion layer is provided in form of a conversion tile with a continuous layer for a number of detector tiles. According to a further example, a number of conversion tiles are provided for one detector tile. In other words, different rations of the conversion layer tiles, or panel elements, to the detector tiles is provided, such as a ratio of smaller than 1, ratio of 1:1, and a ratio of larger than 1.

According to a further example, the X-ray conversion layer 84 is of a scintillator type, wherein the pixels in the pixel array each comprise a light-sensing element to detect light generated in the scintillator layer by X-ray influence.

For example, the light-sensing element is a photo-diode.

It is explicitly noted, that the detector is provided for medical imaging applications according to a further example.

The detector may also be provided for non-medical imaging applications, such as non-destructing material testing or security purposes, such as luggage and goods screening, in relation with an X-ray detector.

Figure 9:
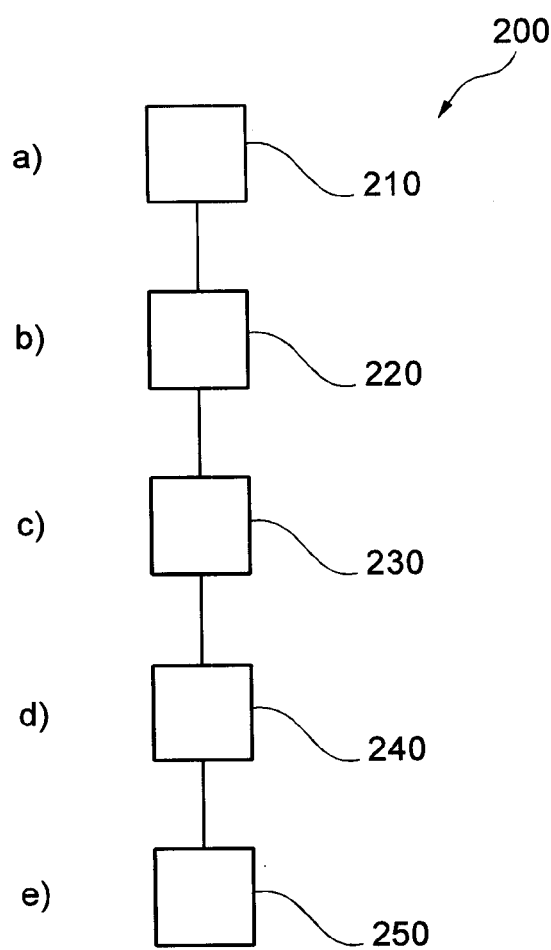
FIG. 9 shows a method for providing a detector tile for a seamless detector surface with a continuous pixel array according to an exemplary embodiment of the present invention.

FIG. 9 shows a method 200 for providing a detector tile for a seamless detector surface with a continuous pixel array, comprising the following steps: In a first step 210, a wafer comprising a flat primary substrate and a surface layer with a circuitry is provided. The wafer comprises a first portion with a circuitry arrangement, which comprises a number of detector pixels providing a pixel array on the surface layer, and at least one second portion with peripheral electronics, wherein the first portion is separated from the at least one second portion by at least one intermediate portion. In a second step 220, a patterned layer of at least one connecting wiring comprising a number of electric leads is formed. The electric leads connect the circuitry arrangement with the pixels with the peripheral electronics. The patterned layer is formed on the front surface of the wafer bridging the intermediate portion. In a third step 230, wafer material in the at least one intermediate portion is removed. In a fourth step 240, wafer material of the first portion is removed such that at least one connection opening is provided in the surface layer and the flat primary substrate at least at one edge of the detector tile, which connection opening is leading from the surface layer to the rear of the substrate for guiding the electric leads between the pixels and the peripheral electronics. In a fifth step 250, the at least one second portion with peripheral electronics is moved to the rear of the wafer, wherein the at least one connecting wiring is guided through the at least one connection opening.

The first step 210 is also referred to as step a), the second step 220 as step b), the third step 230 as step c), the fourth step 240 as step d), and the fifth step 250 as step e).

According to a further example, not further shown, at least two detector tiles are provided according to steps a) to e), wherein the at least two detector tiles are arranged in a common plane abutting each other such that a seamless detector surface is provided with the continuous pixel array.

According to a further example of the present invention, it is proposed to use a polyimide-based patterned layer with metallization patterns that can act as hinges to connect separated silicon sub-tiles such that the silicon tile can be electrically connected via the back. The hinges electrically connect the pixel of an array on the front side of the tile. All these connections are then centralized at a limited number of areas located at the border of the tile. At a main area, a pixel is replaced by a hole extending through the thickness of a tile (front to rear side). Centralized connections are passed from the front to the rear side of the tile through such a hole. It is noted that a very limited number of individual pixels are sacrificed along the sides of each tile for such passage.

Besides, all tiles can be read out individually using additional small supporting silicon tiles and electrical read-out circles that are electrically connected to the electronic boards using for example connectors and/or flex foils.

It is further noted that the above mentioned examples refer to a flat arrangement of adjacent detector tiles. Of course, it is also possible to arrange adjacent tiles abutting each other in a common surface, wherein the common surface may be a flat surface, or a three-dimensionally shaped surface, such as, for example, a section of a spherical surface. In such embodiment, the detector tiles themselves can be provided as flat detector tiles, each focusing on a common focusing point, which for example is applicable for X-ray radiation applications with a cone-beam of X-rays, for example in CT applications.

According to a further example, the detector tiles arrangement may be provided in a three-dimensional shaped form, for example as a section of a spherical surface. Thus, adjacent tiles can be provided contacting each other along the edges, forming a continuous, for example, spherical surface, such as a facet-like surface comprised of flat sub-portions.

According to a further example, the detector tiles themselves may have a three-dimensional shaped form instead of being flat tiles. Thus, smooth spherical detector surfaces are provided. For example, organic material may be used for the primary and also the secondary substrate.

It is further noted that the above mentioned examples show connection openings on only two opposing sides, but the invention also relates to providing connection openings on more than two sides, for example on three sides or four sides. Further, the connection openings may also be provided on two connecting sides, for example.

It is further noted that the detector tiles are shown as squares or rectangles. However, also other forms of the detector tiles can be provided, for example hexagonal structures, thus forming a so-to-speak honeycomb structure. However, considering the application of the circuitry arrangement with the pixels on the surface layer, a rectangular form of the detector tile provides a complete coverage with detector pixels, except for the connection openings, when applying square-like detector pixels.

It is further noted that instead of the C-arm imaging system shown in FIG. 1, the invention is also provided for other types of X-ray examination apparatus, for example for CT imaging systems, or non-movable X-ray imaging systems.

It has to be noted that embodiments of the invention are described with reference to different subject-matters. In particular, some embodiments are described with reference to method type claims, whereas other embodiments are described with reference to device type claims.

However, a skilled person in the art will gather from the above description that, unless otherwise notified, in addition to any combination of features belonging to one type of subject-matter, also any combination between features relating to different subject-matters is considered to be disclosed with this application. However, all features can be combined, providing synergetic effects that are more than the simple summation of the features. While the invention has been illustrated and described in detail in the drawings and foregoing description, such illustration and description are to be considered as illustrative or exemplary and not restrictive. The invention is not limited to the disclosed embodiments. Other variations to the disclosed embodiments can be understood and effected by those skilled in the art in practicing the claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A detector tile, comprising:
   a flat primary substrate;
   a surface layer with a circuitry arrangement,
       wherein the surface layer is arranged on a front side of the flat primary substrate covering the flat primary substrate, and wherein the circuitry arrangement comprises detector pixels providing forming a pixel array; and
   a connection opening provided in the surface layer and the flat primary substrate at least at one edge of the detector tile, wherein the connection opening leads from the surface layer to a rear of the flat primary substrate for guiding electrical connection elements between the front side and the rear of the flat primary substrate,
   wherein at all circumferential edges of the detector tile, the surface layer comprises portions with detector pixels, wherein the portions extend to the circumferential edges,
   wherein the connection opening comprises first connection openings at a first edge of the flat primary substrate and second connection openings at a second edge of the flat primary substrate opposite the first edge, and
   wherein the first and second connection openings are provided in an alternating arrangement between the first and second edges of the detector tile.

2. The detector tile according to claim 1, wherein the connection opening consumes an area of a single pixel.

3. The detector tile according to claim 1, wherein a first offset is provided between each of the first connection openings and a second offset is provided between each of the second connection openings, wherein the first offset has a first length along the first edge and the second offset has a second length along the second edge, and wherein the first length is different from the second length for providing the alternating arrangement of the first and the second connection openings.

4. The detector tile according to claim 1, further comprising peripheral electronics on a secondary substrate arrangement, wherein the secondary substrate arrangement is arranged on the rear of the flat primary substrate; and
   at least one connecting wiring comprising electric leads connecting the circuitry arrangement on the surface layer with the peripheral electronics, wherein the at least one connecting wiring is guided through the connection opening.

5. The detector tile according to claim 1, wherein the connection opening comprises a plurality of connection openings provided at least on two sides of the detector tile, and
   wherein the plurality of connection openings is arranged such that the detector tile is abuttable on at least three sides for providing a seamless detector surface.

6. The detector tile according to claim 1, wherein the pixel array comprises a detector tile grid, and wherein edge pixels of the detector pixels arranged along at least one side of the detector tile have a reduced size relative to non-edge pixels of the detector pixels in a direction transverse to an edge of the detector tile such that an outmost edge of the detector tile is arranged within a respective grid field of the pixel array.

7. A detector panel arrangement, comprising:
   detector tiles, wherein each detector tile comprises:
       a flat primary substrate;
       a surface layer with a circuitry arrangement, wherein the surface layer is arranged on a front side of the flat primary substrate covering the flat primary substrate, and wherein the circuitry arrangement comprises detector pixels forming a pixel array; and
       connection openings provided in the surface layer and the flat primary substrate at least at one edge of the detector tile, wherein the connection openings lead from the surface layer to a rear of the flat primary substrate for guiding electrical connection elements between the front side and the rear of the flat primary substrate,
   wherein at all circumferential edges of the detector tile, the surface layer comprises portions with detector pixels, wherein the portions extend to the circumferential edges,
   wherein the detector tiles are arranged in a common plane abutting each other such that a seamless detector surface is provided with a continuous pixel array,
   wherein the continuous pixel array is only partially interrupted by the connection openings, and
   wherein the connection openings at the at least one edge of the detector tiles are arranged in an alternating arrangement on an edge of a first detector tile with respect to an edge of a second detector tile adjacent to the edge of the first detector tile.

8. The detector panel according to claim 7, wherein adjacent detector tiles each comprises adjacent pixel portions arranged such that portions, wherein the adjacent pixel portions comprise a transition portion with a continuous pixel array sub-portion.

9. The detector panel according to claim 7, wherein the connection openings of adjacent detector tiles are arranged displaced to each other.

10. An X-ray detector comprising:
    a detector panel arrangement; and
    an X-ray conversion layer in front of the detector panel;
    wherein the detector panel arrangement comprises:
    detector tiles, wherein each detector tile comprises:
        a flat primary substrate;
        a surface layer with a circuitry arrangement, wherein the surface layer is arranged on a front side of the flat primary substrate covering the flat primary substrate, and wherein the circuitry arrangement comprises detector pixels forming a pixel array; and
        connection openings provided in the surface layer and the flat primary substrate at least at one edge of the detector tile, wherein the connection openings lead from the surface layer to a rear of the flat primary substrate for guiding electrical connection elements between the front side and the rear of the flat primary substrate,
    wherein at all circumferential edges of the detector tile, the surface layer comprises portions with detector pixels, wherein the portions extend to the circumferential edges,
    wherein the detector tiles are arranged in a common plane abutting each other such that a seamless detector surface is provided with a continuous pixel array,
    wherein the continuous pixel array is only partially interrupted by the connection openings, and wherein the connection openings at the at least one edge of the detector tiles are arranged in an alternating arrangement on an edge of a first detector tile with respect to an edge of a second detector tile adjacent to the edge of the first detector tile, and wherein the X-ray conversion layer is configured to provide signals to the detector panel upon being radiated by X-rays; wherein the signals are adapted to electrically activate the pixels in the surface layer of the detector tiles.

11. X-ray detector according to claim 10, wherein the X-ray conversion layer is of a direct conversion type; wherein for each pixel of the surface, the X-ray radiation is converted into an electrical signal supplied to the respective pixel.

12. X-ray detector according to claim 11, wherein the electrical signal is provided by a conversion material arranged on the pixel of the surface layer; wherein between the pixel and the conversion material an isolating layer is provided and wherein the pixels are provided with an electrode passing through the isolating layer up to the surface providing electrical connection with the conversion material.

13. X-ray detector according to claim 10, wherein the X-ray conversion layer is of a scintillator type; wherein the pixels in the pixel array each comprise a light-sensing element to detect light generated in the scintillator layer by X-ray influence.

14. An X-ray imaging system comprising:
an X-ray source;
the X-ray detector of claim 10; and
a processing unit;
wherein the processing unit is configured at least to correct for missing image information in the area of the connection openings of the continuous pixel array.

15. The detector tile according to claim 1, wherein the connection opening comprises a plurality of connection openings, and wherein the plurality of connection openings have at least one of different opening widths and different depths.

16. The detector tile according to claim 1, wherein the connection opening comprises a plurality of connection openings, and wherein a distance between adjacent connection openings at the at least one edge of the detector tile is larger than an opening width of the connection opening.

* * * * *